(12) United States Patent
Martins et al.

(10) Patent No.: US 8,252,957 B2
(45) Date of Patent: Aug. 28, 2012

(54) PROCESS FOR OBTAINING THE CRYSTALLINE FORM V OF AGOMELATINE

(75) Inventors: Damien Martins, Rouen (FR); Gerard Coquerel, Boos (FR); Julie Linol, Rouen (FR); Pascal Langlois, Saint Jean de la Neuville (FR)

(73) Assignee: Les Laboratoires Servier, Suresnes Cedex (FR)

( * ) Notice: Subject to any disclaimer, the term of this patent is extended or adjusted under 35 U.S.C. 154(b) by 515 days.

(21) Appl. No.: 12/462,470

(22) Filed: Aug. 4, 2009

(65) Prior Publication Data
US 2010/0036165 A1    Feb. 11, 2010

(30) Foreign Application Priority Data

Aug. 5, 2008 (FR) ...................... 08 04466

(51) Int. Cl.
*C07C 233/05*    (2006.01)

(52) U.S. Cl. ........................ 564/219; 514/630
(58) Field of Classification Search .................. 564/219; 514/630
See application file for complete search history.

(56) References Cited

U.S. PATENT DOCUMENTS
2008/0280991 A1* 11/2008 Gant et al. .................... 514/630

FOREIGN PATENT DOCUMENTS
EP    1564202    8/2005
EP    1752443    2/2007

OTHER PUBLICATIONS

B. Tinant, et al., "N-[2-(7-methoxy-1-naphthyl)ethyl] acetamid e, a potent melatonin analog" ACTA Crystallographica Section C, vol. C50, No. 6, p. 907-910, Jan. 1, 1994.
French Preliminary Search Report for FR/08.4466 of Mar. 13, 2009.

* cited by examiner

*Primary Examiner* — Shailendra Kumar
(74) *Attorney, Agent, or Firm* — Hueschen and Sage

(57) ABSTRACT

Process for obtaining the crystalline form V of the compound of formula (I):

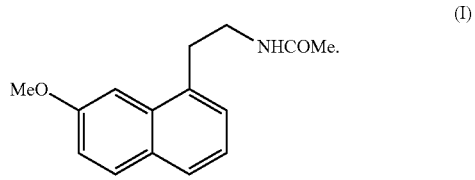

5 Claims, No Drawings

PROCESS FOR OBTAINING THE CRYSTALLINE FORM V OF AGOMELATINE

The present invention relates to a new process for obtaining the crystalline form V of agomelatine, or N-[2-(7-methoxy-1-naphthyl)ethyl]acetamide, of formula (I):

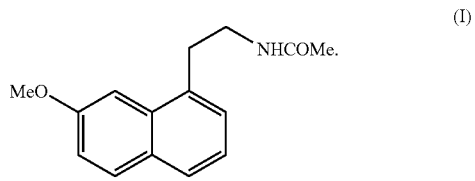

Agomelatine, or N-[2-(7-methoxy-1-naphthyl)ethyl]acetamide, has valuable pharmacological properties.

It has, in fact, the double characteristic of being, on the one hand, an agonist of receptors of the melatoninergic system and, on the other hand, an antagonist of the $5\text{-HT}_{2C}$ receptor. These properties provide it with activity in the central nervous system and, more especially, in the treatment of major depression, seasonal affective disorder, sleep disorders, cardiovascular pathologies, pathologies of the digestive system, insomnia and fatigue due to jet-lag, appetite disorders and obesity.

Agomelatine, its preparation and its use in therapeutics have been described in European Patent EP 0 447 285.

In view of the pharmaceutical value of this compound, it has been of prime importance to obtain it with excellent purity and especially in a perfectly reproducible form that has valuable characteristics allowing its storage for long periods without particular requirements for temperature, light, humidity or oxygen levels.

The Patent Application EP 1 752 443 describes a well-defined crystalline form of agomelatine, the crystalline form V, characterised by the following X-ray powder diffraction diagram thereof, measured using a Siemens D5005 diffractometer (copper anticathode) and expressed in terms of interplanar distance d, Bragg's angle 2 theta, and relative intensity (expressed as a percentage in relation to the most intense line):

| 2-Theta (°) exp. | d (Å) exp. | Intensity (%) |
|---|---|---|
| 9.84 | 8.979 | 17 |
| 12.40 | 7.134 | 15 |
| 13.31 | 6.646 | 19 |
| 15.14 | 5.848 | 18 |
| 15.98 | 5.543 | 18 |
| 16.62 | 5.329 | 19 |
| 17.95 | 4.939 | 100 |
| 18.88 | 4.697 | 65 |
| 20.49 | 4.332 | 24 |
| 20.99 | 4.228 | 34 |
| 23.07 | 3.852 | 39 |
| 23.44 | 3.792 | 36 |
| 24.28 | 3.663 | 58 |
| 25.10 | 3.545 | 19 |
| 26.02 | 3.422 | 15 |
| 26.82 | 3.322 | 19 |
| 27.51 | 3.239 | 16 |

This perfectly defined crystalline form, which is obtained in reproducible manner, has highly valuable morphological properties with, especially, a specific surface area that is much greater than for the other described forms. Nevertheless, it has stability over time which is rather short and, in all cases, less than 6 months.

The Applicant has now developed a new process for obtaining agomelatine in the crystalline form V in perfectly reproducible manner, whereby its stability over time is increased. This new process accordingly makes it possible to obtain agomelatine in the crystalline form V with properties that are compatible with the pharmaceutical use thereof. It used to be possible to obtain the form V only by so-called "high-energy" milling or by means of seeding using that structurally pure form which had been obtained by milling. The Applicant has now discovered, surprisingly, that it is possible to obtain this form by means of spray drying. Spray drying is in fact a technique customarily used for obtaining solid particles in small sizes. Often, the resulting material is amorphous (Amorphous state, Polymorphism in pharmaceutical industry, Ed. R. Hilfiker, Wiley-VCH Weinheim 2006, Chapter X, p. 259-285, S. Petit and G. Coquerel). In contrast thereto, in the present invention spray drying makes it possible to obtain a well-defined crystalline form, the form V, which moreover has, however, much better stability over time.

More specifically, the present invention relates to a new process for obtaining agomelatine of formula (I) in the crystalline form V, which process is characterised in that a solution of agomelatine that has been dissolved in one or two solvents which are miscible in any proportion and whose boiling point is less than 120° C. is atomised in an spray dryer.

Spray drying is a technique commonly used in the agricultural, food and pharmaceutical sectors to dry a solution that is sprayed through a hot gas. In practice, the gas used for drying the solution is air but certain pharmaceutical production methods using organic solvents require an inert gas as a drying gas, thereby avoiding certain decomposition processes.

The crystallisation operations according to the present invention are preferably carried out by means of a spray dryer. Even more preferably, the atomisation according to the invention is carried out according to the principle of atomisation by means of a nozzle with parallel current flow and more preferably with co-current flow, that is to say the sprayed solution and the drying gas flow in the same direction.

Advantageously, the gas used is compressed air or an inert gas such as, for example, nitrogen.

Preferred solvents for the process according to the invention are ethanol, water, isopropyl ether, methanol, ethyl acetate or acetone.

The minimum concentration of the agomelatine solution used is 5 g/l and, more preferably, a 10 g/l solution is used.

Advantageously, the inlet temperature for the process according to the invention is from 70° C. to 120° C.

In the crystallisation process according to the invention it is possible to use agomelatine of formula (I) obtained by any process.

The Examples hereinbelow illustrate the invention but do not limit it in any way.

EXAMPLE 1

Crystalline form V of N-[2-(7-methoxy-1-naphthyl)ethyl]acetamide

A 10 g/l solution of agomelatine in an ethanol/isopropyl ether mixture (50/50: v/v) is introduced into an atomiser of the BUCHI 190 Mini Spray Dryer type. The inlet temperature of the drying chamber is 90° C., and the outlet temperature is 66° C. The atomised powder is recovered in the collecting bowl and has been characterised by the following crystallographic data:

1) diagram obtained using the Siemens D5005 diffractometer with an angular range of 3°-30° in terms of 2θ, a step of 0.04° and 4 s per step:

crystal structure of unit cell: monoclinic,
unit cell parameters: a=11.967 Å, b=17.902 Å, c=15.423 Å, β=124.5°
space group: $P2_1/n$
number of molecules in the unit cell: 8 (Z'=2)
volume of the unit cell: $V_{unit\ cell}$=2720.0 Å$^3$ 2) the following X-ray powder diffraction diagram, measured using a Siemens D5005 diffractometer (copper anticathode) and expressed in terms of interplanar distances d, Bragg's angles 2 theta, and relative intensities (expressed as a percentage in relation to the most intense line):

| 2-Theta (°) exp. | d (Å) exp. | Intensity (%) | 2-Theta (°) calc. |
|---|---|---|---|
| 9.84 | 8.979 | 17 | 9.85 |
| 12.40 | 7.134 | 15 | 12.46 |
| 13.31 | 6.646 | 19 | 13.33 |
| 15.14 | 5.848 | 18 | 15.16 |
| 15.98 | 5.543 | 18 | 15.91 |
| 16.62 | 5.329 | 19 | 16.66 |
| 17.95 | 4.939 | 100 | 17.96 |
| 18.88 | 4.697 | 65 | 18.93 |
| 20.49 | 4.332 | 24 | 20.52 |
| 20.99 | 4.228 | 34 | 20.99 |
| 23.07 | 3.852 | 39 | 23.11 |
| 23.44 | 3.792 | 36 | 23.48 |
| 24.28 | 3.663 | 58 | 24.27 |
| 25.10 | 3.545 | 19 | 25.18 |
| 26.02 | 3.422 | 15 | 26.02 |
| 26.82 | 3.322 | 19 | 26.85 |
| 27.51 | 3.239 | 16 | 27.56 |

EXAMPLE 2

Stability Over Time of the Crystalline Form V, Obtained by Atomisation, of N-[2-(7-methoxy-1-naphthyl)ethyl]acetamide A sample of 1 g of the compound obtained in Example 1 was placed under customary storage conditions: ambient pressure and temperature. After 21 months, the diffractogram of the sample that was obtained had not changed and remained characteristic of the form V obtained.

The invention claimed is:
1. A process for obtaining crystalline form V of agomelatine of formula (I):

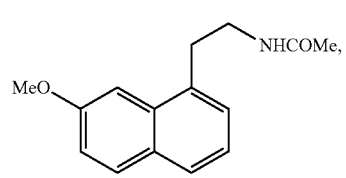

(I)

wherein a solution of agomelatine that has been dissolved in one or two solvents which are miscible in any proportion and whose boiling point is less than 120° C., wherein the solvent(s) is selected from ethanol, water, isopropyl ether, methanol, ethyl acetate and acetone, is atomised in a spray dryer.

2. The process of claim 1, wherein the crystalline form V of the compound of formula (I) exhibits essentially the following X-ray powder diffraction diagram, measured using a diffractometer (copper anticathode) and expressed in terms of interplanar distances d, Bragg's angles 2 theta, and relative intensities (expressed as a percentage in relation to the most intense line):

| 2-Theta (°) exp. | d (Å) exp. | Intensity (%) | 2-Theta (°) calc. |
|---|---|---|---|
| 9.84 | 8.979 | 17 | 9.85 |
| 12.40 | 7.134 | 15 | 12.46 |
| 13.31 | 6.646 | 19 | 13.33 |
| 15.14 | 5.848 | 18 | 15.16 |
| 15.98 | 5.543 | 18 | 15.91 |
| 16.62 | 5.329 | 19 | 16.66 |
| 17.95 | 4.939 | 100 | 17.96 |
| 18.88 | 4.697 | 65 | 18.93 |
| 20.49 | 4.332 | 24 | 20.52 |
| 20.99 | 4.228 | 34 | 20.99 |
| 23.07 | 3.852 | 39 | 23.11 |
| 23.44 | 3.792 | 36 | 23.48 |
| 24.28 | 3.663 | 58 | 24.27 |
| 25.10 | 3.545 | 19 | 25.18 |
| 26.02 | 3.422 | 15 | 26.02 |
| 26.82 | 3.322 | 19 | 26.85 |
| 27.51 | 3.239 | 16 | 27.56. |

3. The process of claim 1, wherein the solvents used are ethanol and isopropyl ether.
4. The process of claim 1, wherein the spray dryer employs nitrogen.
5. The process of claim 1, wherein the minimum concentration of the agomelatine solution used is 5 g/l.

* * * * *